(12) United States Patent
Salyer

(10) Patent No.: US 6,409,732 B1
(45) Date of Patent: Jun. 25, 2002

(54) TOOL DRIVER

(75) Inventor: Paul E. Salyer, Warsaw, IN (US)

(73) Assignee: Othy, Inc., Warsaw, IN (US)

( * ) Notice: Subject to any disclaimer, the term of this patent is extended or adjusted under 35 U.S.C. 154(b) by 0 days.

(21) Appl. No.: 09/349,381

(22) Filed: Jul. 9, 1999

(51) Int. Cl.[7] .............................................. A61B 17/58
(52) U.S. Cl. ...................................................... 606/91
(58) Field of Search .............................. 606/91, 80, 81, 606/82; 408/189, 227, 713, 226, 231; 470/97; 29/451, 48; 175/295; 451/48; 433/165

(56) References Cited

U.S. PATENT DOCUMENTS

| | | | | |
|---|---|---|---|---|
| 1,122,786 A | * | 12/1914 | Moore | 408/226 |
| 2,529,396 A | * | 11/1950 | Hunt | 408/226 |
| 2,678,826 A | * | 5/1954 | Nick | 408/226 |
| 2,785,673 A | | 3/1957 | Anderson | |
| 3,053,118 A | * | 9/1962 | Lavallee | 408/226 |
| 3,612,359 A | * | 10/1971 | Sundholm | 222/309 |
| 3,633,583 A | * | 1/1972 | Fishbein | 606/91 |
| 3,667,456 A | | 6/1972 | Charnley | |
| 3,702,611 A | * | 11/1972 | Fishbein | 606/91 |
| 4,023,572 A | | 5/1977 | Weigand et al. | |
| 4,072,441 A | | 2/1978 | LaPointe | |
| 4,116,200 A | | 9/1978 | Braun et al. | |
| 4,131,116 A | * | 12/1978 | Hedrick | 128/305 |
| 4,242,684 A | * | 12/1980 | Wolverton | 343/715 |
| 4,811,632 A | | 3/1989 | Salyer | |
| 5,100,267 A | | 3/1992 | Salyer | |
| 5,116,165 A | | 5/1992 | Salyer | |
| 5,236,433 A | * | 8/1993 | Salyer | 606/91 |
| 5,299,893 A | | 4/1994 | Salyer et al. | |
| 5,709,688 A | | 1/1998 | Salyer | |

FOREIGN PATENT DOCUMENTS

| | | |
|---|---|---|
| DE | 2500958 | 1/1975 |
| GB | 666621 | 2/1952 |
| SU | 166449 | 12/1965 |

* cited by examiner

Primary Examiner—David O. Reip
Assistant Examiner—(Jackie) Tan-Uyen T. Ho
(74) Attorney, Agent, or Firm—Taylor & Aust, P.C.

(57) ABSTRACT

A tool driver having a shaft with a longitudinal axis and opposite ends. A boss is secured at one of the shaft ends by which the tool driver is connected to a rotary tool. A tool collate is secured to the other of the shaft ends by which the tool driver may be driven by a surfical hand piece having a chuck in which the collate may be positioned. The boss is equipped with a securing device of the bayonet type having a latch mechanism which holds the rotary tool on the boss coaxially of the driver during use. The securing device has a tapered bore extending from the distal end of the boss axially of the shaft. The rotary tool has a diametral bar extending across a bottom tool driver opening with a centrally located circular disk therein. The disk of the rotary tool fits within the bore of the tool shaft boss so as to concentrically locate the rotary tool and the tool shaft on the same axis. The latch mechanism holds the tool driver and the tool together in this position, whereby rotary tools of a multitude of sizes can be secured concentrically to the tool shaft without holding a plurality of critical tolerances when machining the bayonet type securing device or the rotary tool bottom bar.

19 Claims, 4 Drawing Sheets

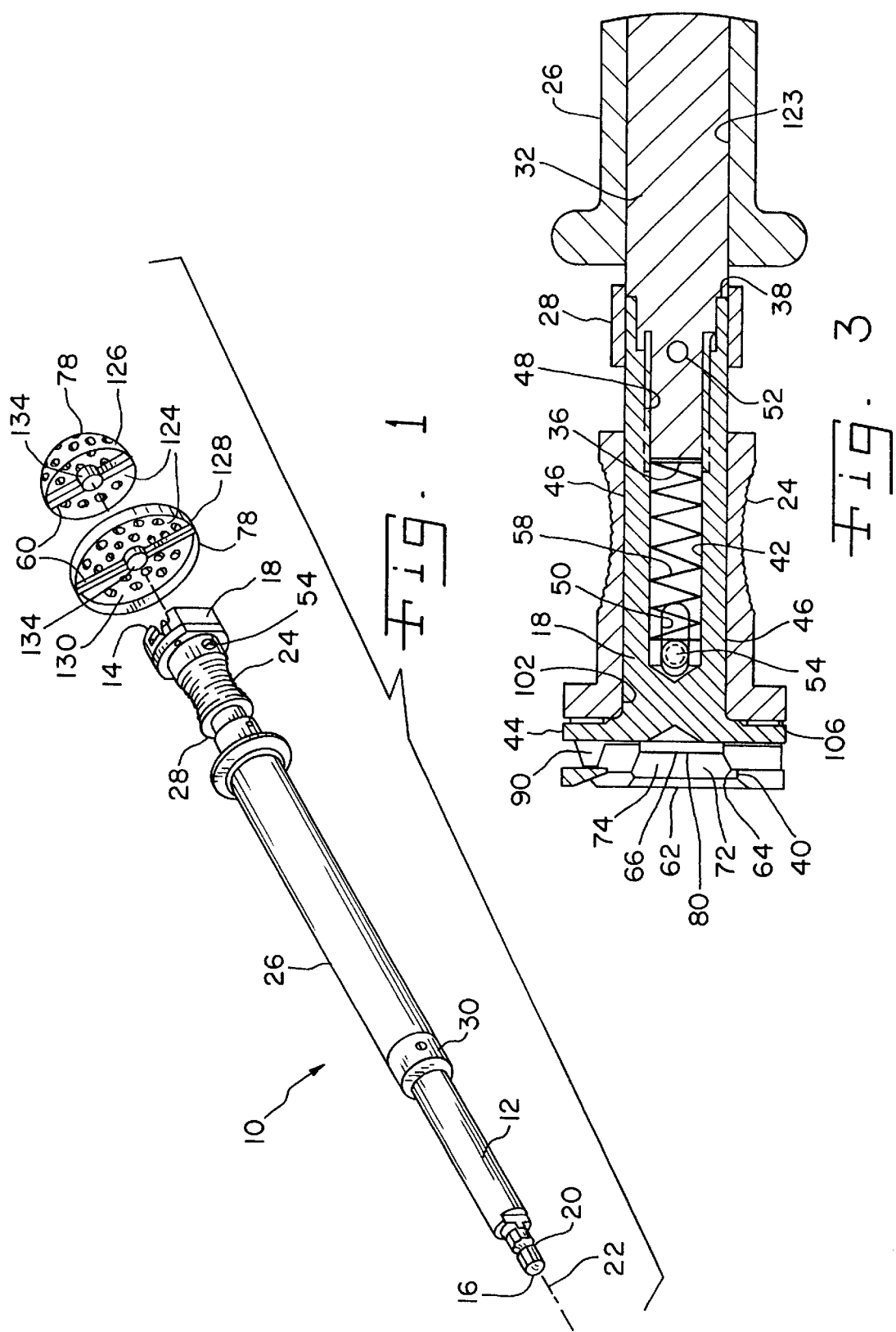

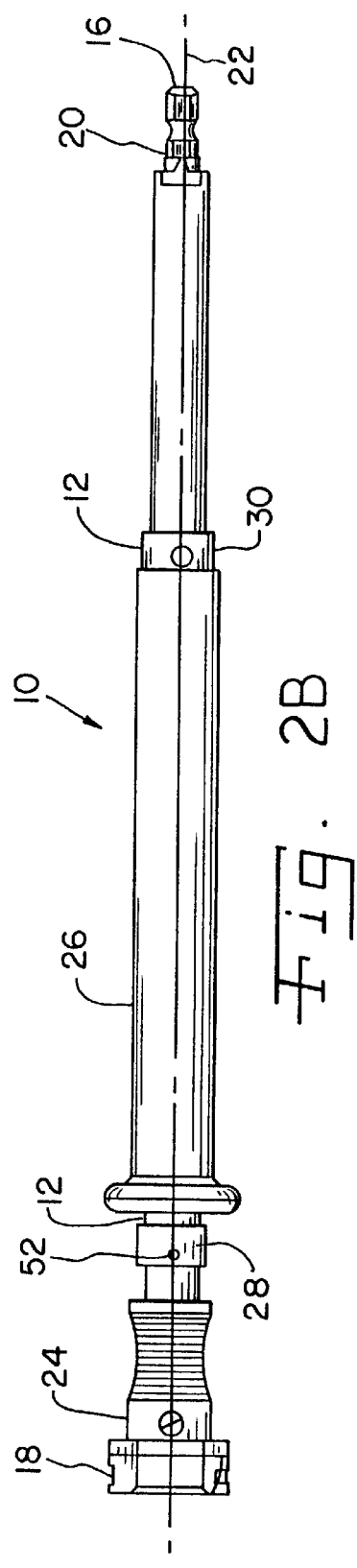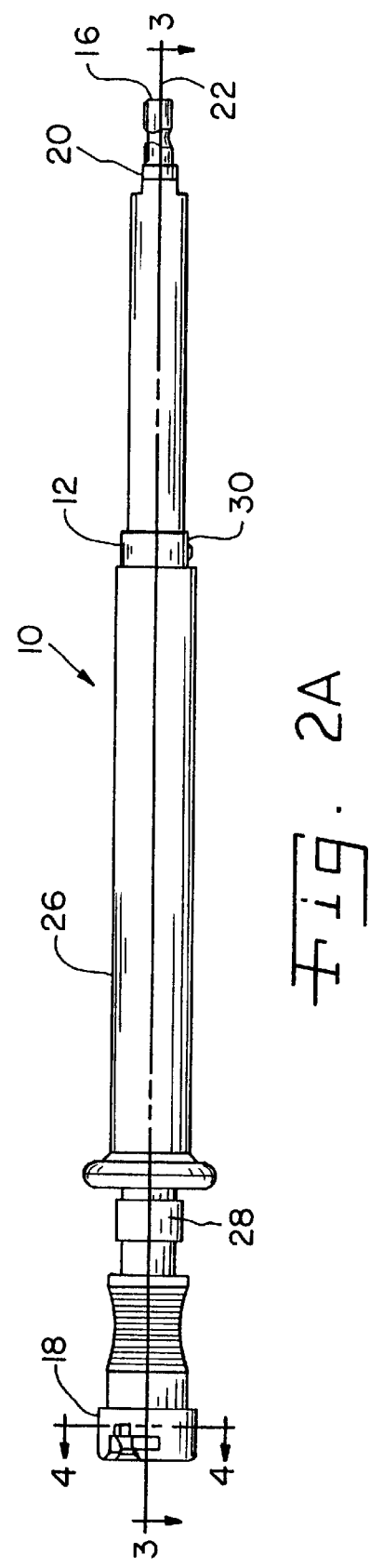

TOOL DRIVER

BACKGROUND OF THE INVENTION

The present invention pertains to tool drivers and holders for rotary tools, and more particularly, to a new and improved tool driver suitable for driving acetabular reamer cups and patella cutters and other surgical tools of any size which is easily cleaned and held and guided to rotate in true concentricity with the tool driver.

Patella cutters and acetabular reamer cups are surgical tools which are used in surgery for the insertion of artificial joints. Acetabular reamer cups are used to cut hemispherical cavities in pelvis bones for the insertion of artificial hip joints. Patella cutters are used to shape the underside of the patella or knee cap during knee replacement surgery. Patella cutters have a complex arrangement of precisely shaped cutting edges spirally arranged around an axis of rotation for cutting the patella. Acetabular reamer cups have a complex arrangement of cutting edges spirally arranged on a spherical surface around the axis of rotation of the cup. Both acetabular reamers and patella cutters perform better when rotated precisely about the axis around which these cutting edges are positioned by design. Additionally precise tolerances cannot be achieved without precise axial rotation as designed.

It is therefore highly desirable to provide a new and improved tool driver. It is also highly desirable to provide a new and improved tool driver which can be used with acetabular reamer cups, patella cutters and like rotary tools. It is also highly desirable to provide a new and improved tool driver by which rotary tools may be driven about the tool driver's longitudinal axis with preciseness such that all of the cutting edges of the rotary tool function as designed.

Acetabular reamer cups also come in a full range of sizes. These sizes range from about 36 millimeters in diameter to about 72 millimeters in diameter. In the past, a specific tool driver could only be used with one or few of the sizes of available acetabular reamer cups. Thus, in any operating room there had to be several tool drivers for acetabular reamer cups. It is therefore also highly desirable to provide a new and improved tool driver by which acetabular reamer cups and patella cutters of all sizes can be driven.

Unique to some knee surgery and some hip operations is the utilization of milled bone, tissue and debris as filler to be placed between the artificial insert and the body to assist the healing process. Thus, acetabular reamer cups and patella cutters are mounted on tool drivers in a manner to collect such debris for such use. It is therefore, also highly desirable to provide a new and improved tool driver on which the rotary tools of the type which collect milled bone tissue and other debris for use as filler can be used.

In all surgery utilizing rotary tools, rotary tools such as those driven by rotary tool drivers must be separable from their tool drivers to replace or sharpen as required. It may also be necessary to change tools during an operation, thus, both the rotary tools and the tool drivers must at times be cleaned, sterilized and reused. Thus, it is therefore also highly desirable to provide a new and improved tool driver which can be easily cleaned, sterilized and reused.

Some previous tool drivers grip the tool utilizing opposed pins, flanges and slots, or opposed spring loaded ball catches, or other such devices. These devices represent a problem in that the catches tend to trap dried blood and other debris which are very difficult to remove during a cleaning process. It is therefore also highly desirable to provide a new and improved tool driver which is simple in construction, easy to use and does not have opposed pins, flanges, slots and other devices in which to catch debris and render the tool driver difficult to clean, sterilize and reuse.

An additional problem is that unless tolerances of tools and tool drivers are made very close, at a greatly increased cost, there is considerable free play between the tool and the tool driver. This increased play increases the wear of the cutting edges, makes more difficult the positioning of the tool, renders the tool useless for holding close tolerances, requires the tool not to cut as designed, and there is no possibility of utilizing the rotary tool spinning precisely about its axis as designed. It is therefore, also highly desirable to provide a new and improved tool driver which allows the rotary tool to be utilized spinning precisely about its axis, as designed.

It is also highly desirable to provide a new and improved tool driver in which close tolerances can be held.

Finally, it is highly desirable to provide a new and improved tool driver which has all of the above desired features.

SUMMARY OF THE INVENTION

It is therefore an object of the invention to provide a new and improved tool driver.

It is also an object of the invention to provide a new and improved patella driver which can be used with both acetabular cups, patella cutters and like rotary tools.

It is also an object of the invention to provide a new and improved tool driver by which rotary tools may be driven about the tool drivers longitudinal axis with preciseness such that all of the cutting edges of the rotary tool function as designed.

It is also an object of the invention to provide a new and improved tool driver which acetabular reamer cups of all sizes and patella cutters can be driven.

It is also an object of the invention to provide a new and improved tool driver on which the rotary tools of the type which collect milled bone tissue and other debris for use as filler, can be used.

It is also an object of the invention to provide a new and improved tool driver which can be easily cleaned, sterilized and reused.

It is also an object of the invention to provide a new and improved tool driver which allows the rotary tool to be utilized spinning precisely about its axis as designed.

It is also an object of the invention to provide a new and improved tool driver which is simple in construction, easy to use and does not have opposed pins, flanges, slots and other devices in which to catch debris and render the tool driver difficult to clean, sterilize and reuse.

It is also an object of the invention to provide a new and improved tool driver in which close tolerances can be held.

It is finally an object of the invention to provide a new and improved tool driver which has all of the above desired features.

In the broader aspects of the invention, there is provided a new and improved tool driver having a shaft with a longitudinal axis and opposite ends. A boss is secured at one of the shaft ends by which the tool driver is connected to a rotary tool. A tool collate is secured to the other of the shaft ends by which the tool driver may be driven by a surgical hand piece having a chuck in which the collate may be positioned. The boss is equipped with a securing device of the bayonet type having a latch mechanism which holds the rotary tool on the boss coaxially of the driver during use. In a specific embodiment, the securing device has a tapered bore extending from the distal end of the boss axially of the shaft. The rotary tool has a diametral bar extending across a bottom tool driver opening with a centrally located circular disk therein. The disk of the rotary tool fits within the bore of the tool shaft boss so as to concentrically locate the rotary tool and the tool shaft on the same axis. The latch mechanism holds the tool driver and the tool together in this position, whereby rotary tools of a multitude of sizes can be secured concentrically to the tool shaft without holding a plurality of critical tolerances when machining the bayonet type securing device or the rotary tool bottom bar.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 1 is an exploded perspective view of the tool driver of the invention showing two sizes of acetabular reamer cups and patella cutters exploded therefrom, illustrating the versatility of the new and improved tool driver of the invention;

FIGS. 2A and 2B are side views of the new and improved tool driver of the invention illustrated in FIG. 1 taken perpendicularly with respect to each other;

FIG. 3 is a fragmentary sectional view of the new and improved tool driver of the invention illustrated in FIGS. 1 and 2 taken along the section line 3—3 of FIG. 2A;

DESCRIPTION OF A SPECIFIC EMBODIMENT

Figure 4:
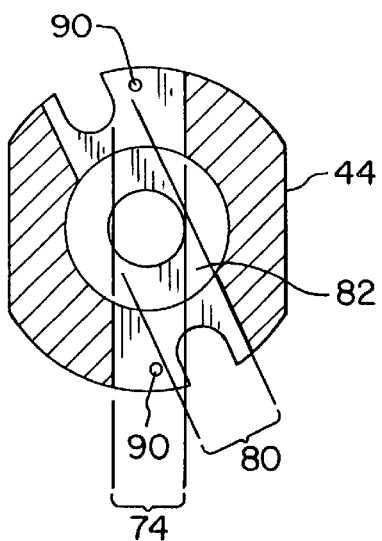
FIG. 4 is a cross-sectional view of the new and improved tool driver of the invention illustrated in FIGS. 1–3 taken substantially along the section line 4—4 of FIG. 2A.

Tool driver 10 comprises a shaft 12 having opposite ends 14, 16 as shown in FIG. 1. At end 14, a boss or head 18 is secured to the shaft 12. At end 16, a tool collate 20 is secured to shaft 12. Shaft 12 has an elongated axis 22 about which both boss or head 18 and collate 20 are positioned and rotated during use. Boss or head 18, collate 20 and shaft 12 are coaxially aligned in end to end relation. Coaxially positioned on the shaft 12 is a tubular trigger 24 and a handle 26. Handle 26 is free to rotate about the shaft 12 between a pair of spaced apart rings 28 and 30 which are secured to shaft 12.

Shaft 12 is made up of head 18, a rod 32 and collate 20. Rod 32 has opposite ends 34 and 36. Similarly, head 18 has opposite ends 38, 40. Head 18 at end 38 has a bore 42 extending axially of head 18. Head 18 has a boss 44 at end 40 and a tubular portion 46 extending from boss 44 to end 38. Bore 42 extends from end 38 to adjacent boss 44. A slot 50 extends transversely of the tubular portion 46 adjacent boss 44 through the bore 48. Slot 50 is elongated in an axial direction as shown.

End 36 of rod 32 is shaped so as to be telescopically received in bore 48 adjacent end 38 of head 18. Rod 32 is secured to head 18 by a pin 52 extending through hole 53 and secured at its opposite ends in ring 28. In other specific embodiments, head 18 and rod 32 or rod 32 and ring 28 may be integrally formed as a single piece. A second pin 52 extends through the ring 30 in the manner above described with regard to the attachment of the head 18 to the rod 32 by ring 28 to secure ring 30 to rod 32 remote from ring 28. Positioned on rod 32 between rings 28 and 30 is tubular handle 26. Handle 26 is coaxial of the rod 32 and is free to rotate independently of rod 32 and to move axially of rod 32 between rings 28, 30.

Similarly positioned on tubular portion 46 of head 18 is trigger 24. Trigger 24 is also free to slide axially of tubular portion 46 between boss 44 and ring 28 except for the engagement of a pin 54 which extends through trigger 24, through slot 50 in head 18, and is secured at its opposite ends to trigger 24.

Figure 6:
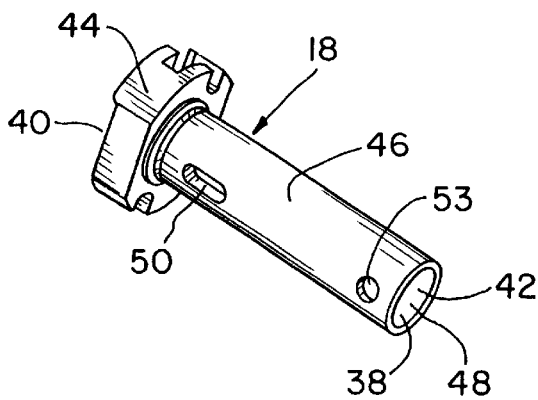
FIG. 6 is a perspective view of the head of the new and improved tool driver of the invention illustrated in FIGS. 1–5.

A spring 58 is positioned within bore 42 of head 18 and compressed between end 36 of rod 32 and pin 54. Pin 54 limits the movement of trigger 24 on tubular portion 46 of head 18 both rotatably about tubular portion 46 and axially of tubular portion 46. See FIGS. 3 and 6.

Figure 5:
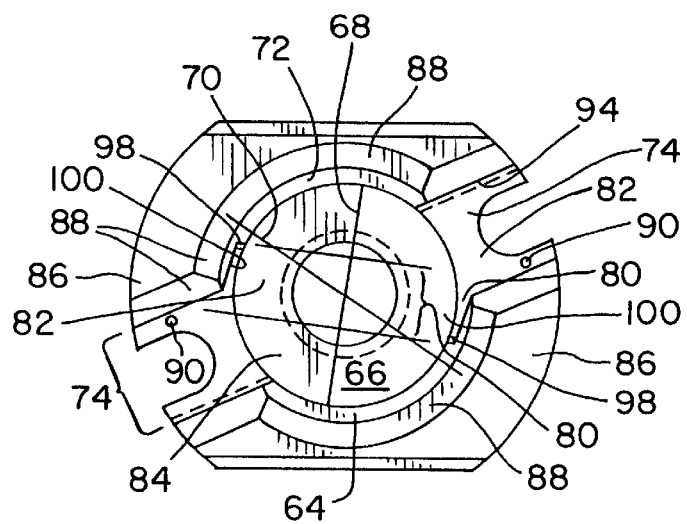
FIG. 5 is a top planar view of the head of the new and improved tool driver of the invention illustrated in FIGS. 1–4.

Boss 44 of head 18 has a distal end 62 and a bore 64 extending axially from distal end 62 of head 18. Bore 64 is tapered as shown in FIGS. 3 and 5 so as to have a bottom 66, a bottom diameter 68, a top diameter 70 and tapered side walls 72. A groove 74 is machined in boss 44 so as to extend diametrically across bore 64 and to have a width which is equal or larger than the diametral rod or bar 60 of the tool 78 which will be used with the tool driver 10. A second diametral groove 80 extends across the bore 64 with a bottom 82 in the same plane as the bottom 84 of the groove 74 and the bottom 66 of the bore 64. Groove 80 is overlaid with a portion 86 of the distal end of the head 18 to form a bayonet type latch. See FIGS. 4 and 5. Groove 74 and bore 64 both have a peripheral tapered surface 88 defining the entry of both bore 64 and groove 74. Bottom 82, 84 have holes 90 therein extending through the head 18 to receive the pins 92 on trigger 24. Groove 74 is bounded on one side by a side wall 94 and on the other side by groove 80. Groove 80 has a floor or bottom 96 in the same plane as bottoms 66, 82 and 84, an upstanding side wall 98, and a ceiling 100. Bottom 96 and ceiling 100 are tapered toward side wall 98 as will be explained hereinafter.

Figure 7:
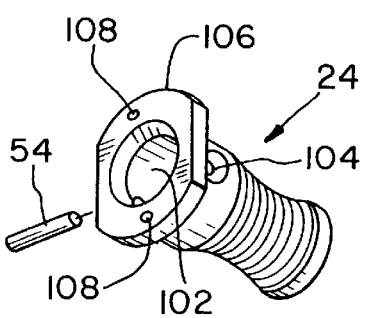
FIG. 7 is a perspective view of the trigger of the new and improved tool driver of the invention illustrated in FIGS. 1–5.
Figure 8:
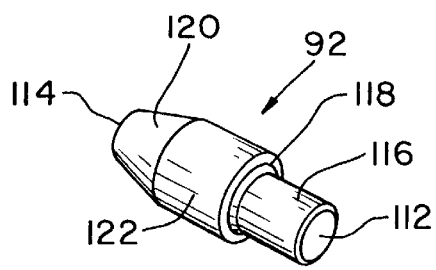
FIG. 8 is a perspective view of the pins which are secured to the trigger of the new and improved tool driver of the invention and which extend upwardly through the head of the new and improved tool driver of the invention.
Figure 9:
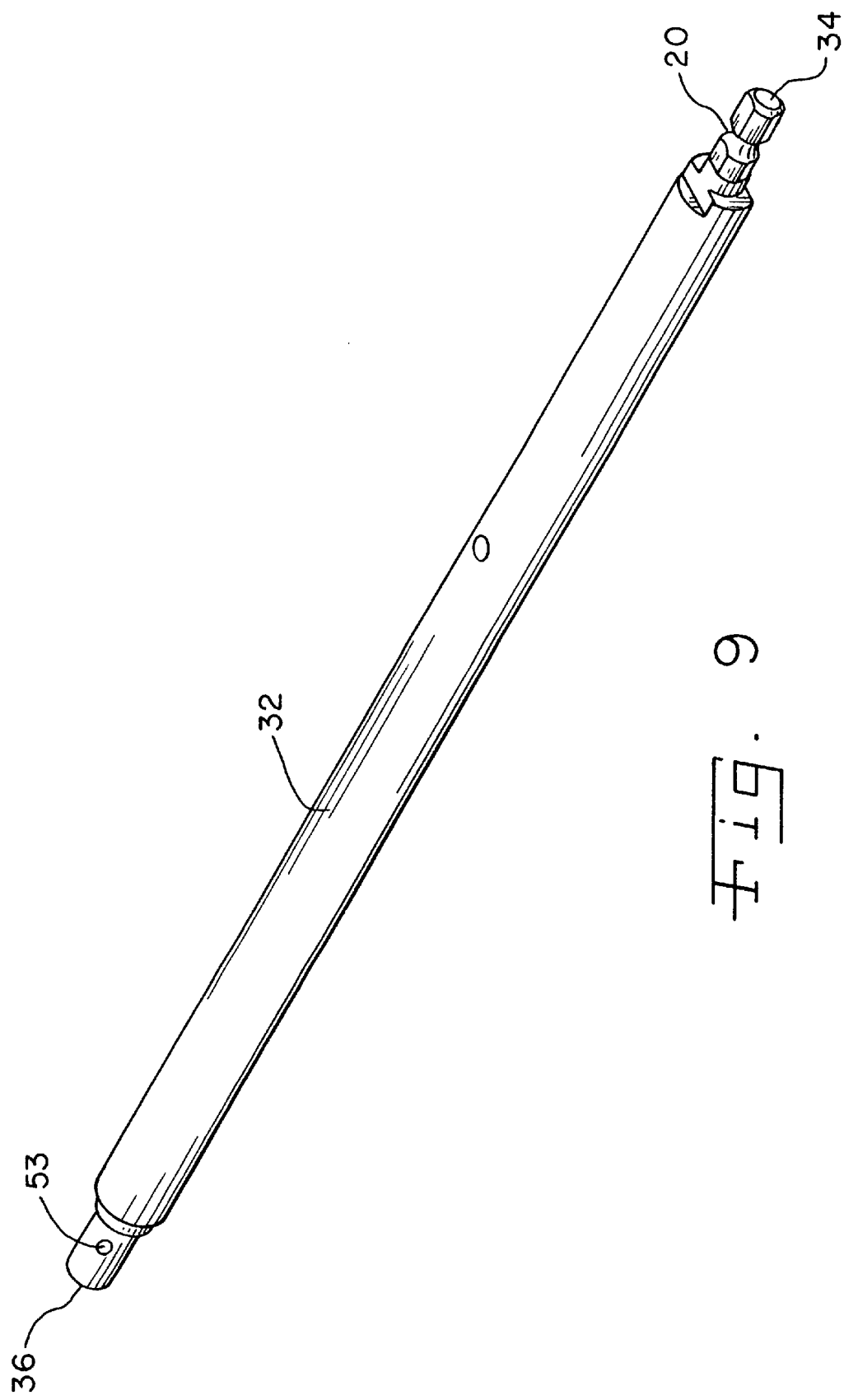
FIG. 9 is a perspective view of the shaft to which is secured the head and on which the trigger and handle is assembled.

As shown in FIGS. 3 and 7, trigger 24 has a bore 102 extending axially therethrough. Transversely of trigger 24 is a pin bore 104 in which the opposite ends of pin 54 are secured. Trigger 24 is slideably mounted upon tubular portion 46 of head 18. Portion 46 is positioned within bore 102. Trigger 24 has a boss 106 which is urged by the spring 58 against boss 44 of the head 18. In the distal end of boss 106 are a pair of diametrically opposed pin bores 108. Pin bores 108 extend axially of trigger 24, and pin bores 108 are positioned with respect to each other such that when pin 54 attaches trigger 24 to head 18, pin bores 108 are coaxial with the pin bores 90 of boss 44 of head 18.

Pins 92 are positioned in pin bores 108. Pins 92 have opposite ends 112, 114. At end 112 is a shank 116 which is secured within a pin bore 108. Shank 116 extends from end 112 and terminates at step 118. Adjacent the opposite end 114 is a tapered surface 120, the purpose of which will be mentioned hereinafter. Between tapered surface 120 and shank 116 is a cylindrical pin portion 122 which is slideably positioned within pin bores 90 of head 18 and boss 44 of head 18. See FIG. 3.

In a specific embodiment, rod 32 is from about 7 to about 11 inches in axial length, has a diameter of approximately 0.375 inches in diameter and made of stainless steel. Handle 26 is from about 5 to about 5.5 inches in length. Bore 123 therethrough is approximately 0.5 inch in diameter. Handle 26 is made of molded polyethylene. Trigger 24 is from about 12.5 inches to about 1.5 inches in axial length, and has a diameter from about 0.375 to about 12.5 inches in diameter and bore 48 extending therethrough is about 0.5 inches in diameter. The pin holes 108 are about 0.1 inches in diameter. Pins 90 are approximately 0.431 inches in diameter. Both trigger 24 and pins 90 are made of stainless steel. Head 18 is approximately 2½ inches long with boss 44 having an axial length of about 1.0625 inches. Head 18 is machined from stainless steel. Bore 48 in tubular portion 46 is approximately 0.25 inches in diameter and bore 64 is approximately 0.550 inches in diameter with a top diameter of 0.637 and a bottom diameter of 0.550 inches. Slot 50 has a width of about 0.125 inches and groove 80 has a width of approximately 0.266 inches. The outside diameter of boss 44 is approximately 1 inch.

In a specific embodiment, diametral rod or bar 60 of the tool 78 is approximately 0.26 inches in width, approximately 0.125 inches in thickness and has a diametral length commensurate with the diameter of the tool 78. The central disc 134 of rod 60 has a diameter of about 0.550 inches and a thickness of about 0.125 inches.

Referring now to FIG. 1, the rotary tool 78 of tool driver 10 is shown to have a hollow interior 124. The rotary tool 78 can be either an acetabular reamer 126 or a patella cutter 128. Each of the rotary tools 78 have a rear opening 130 which provides access to the interior 124 such that milled bone, tissue and other debris may be collected within the interior 124 and removed for use during the surgical procedure as desired. Each of the rotary tools has extending across the opening 130 a diametral bar or rod 60. Equally distant between the ends of the diametral bar 60 is a centering disc 134. Centering disc 134 has a diametral relationship with bore 64, and diametral bar 60 has a diametral relationship with both grooves 74, 80 as will be mentioned hereinafter. Rotary tools 78 are provided in a variety of sizes ranging from 36 millimeters in diameter to 72 millimeters in diameter. Each of these rotary tools, however, have a diametral mounting bar 60 and a centering disc 134 of the same dimensions for reasons to become clear hereinafter.

In operation, the rotary tool 78 to be driven by the tool driver 10 is selected and positioned adjacent the distal end 62 of the boss 44. The diametral mounting bar or rod 60 is aligned with groove 74 and moved axially toward end 16 of the shaft 12. Diametral bar 60 may engage the taper 88 and be guided by the taper 88 into the groove 74. Groove 74, between pin 90 and the groove side 94 opposite pin 90, has a sufficient width to accommodate the bar 60. The centering disc 134 is dimensioned with respect to the bore 64 that it centers the bore 64 and the centering disc 134 of the tool 78 and positions the tool 78 and the shaft 12 coaxially on axis 22, the axis of rotation of the shaft 12. Thus, the diametral periphery of the centering disc 134 may engage the taper 88 and then the wall 72 of the bore 64 to be guided into its coaxial position and to rest on the bottom 66 or thereabouts.

Inasmuch as the groove 74 does not have tapered walls, but the bore 64 does, the difference in the top diameter 70 and the bottom diameter 68 of the bore 64 will function with the centering disc 134 to center the tool 78 coaxially of the shaft 12.

The taper of the bore 64 centers the tool 78 coaxially of the shaft 12 irrespective of the holding of tolerances of either the bore 64 or the centering disc 134. Even if tolerances are held loosely, the tapered sides of bore 64 between the bottom diameter 68 and the top diameter 70 center the centering disc 134 on the axis 22 and position the centering disc coaxially of the shaft 12. Different dimensions of the bore 64 or the centering disc 134 within loose tolerances would position the centering disc 134 at various positions spaced apart from bore bottom 66. However, in each of these positions, the centering disc 134 and the rotary tool 78 would still be coaxial of the shaft 12.

Once the centering disc 134 and the diametral bar 60 are positioned within bore 64 and groove 74, respectively, pins 92 may be retracted by moving the trigger 24 toward end 16 against the resiliency of the spring 58. By moving the trigger 24, the pin 54 is moved toward the end 36 of shaft 12, compressing the spring 58 and retracting the pins 92 into the pin holes 90. With pins 92 retracted, the tool 78 can be rotated with respect to the shaft 12 so as to move the diametral bar 60 from groove 74 into the bayonet-type catch 136 defined by groove 80, its bottom 82, its overlaying portion 86, upstanding groove wall 98 and top wall 100. Bottom 82 and top wall 100 are also tapered, again to make unnecessary close tolerances, to those bar 60 against axial movement therebetween.

Diametral bar 60 can then be held fast within the bayonet catch 136 by releasing the trigger 24 and allowing the spring 58 to urge the trigger 24 against the boss 44 to move the pins 92 back into their at rest position. Pins 92, and specifically the tapered portions 120 thereof, engage the diametral bar 60 and urge the diametral bar 60 toward the wall 98 of the groove 80. By its tapered portion 120, pins alleviate any need for holding close tolerances between the wall 98 and the pin holes 90 or in the width of the diametral bar 60. Additionally, the tolerances between wall 100 and bottom 82 of groove 80 need not be held close, as well as the tolerances of the dimensions of the diametral bar 60, the tolerances between bottom 82 and top wall or ceiling 100, the tolerances between the centering disc 134 and the bore 64, and the tolerances between the diametral bar 60 and the opposite walls 98 of the groove 80 and the tapered pin portion 120 to hold the rotary tool 78 coaxially of the shaft 12 and immovable relative to shaft 12 without such tolerances. Because of the taper of the bore 64 and the taper of the pin 92, lateral movement of the tool 78 with respect to the shaft axis 22 and rotary movement about the shaft axis 22 of the tool 78 is prevented. Axial movement of the diametral bar 60 is prevented by the taper between wall 100 and bottom 82 of groove 80. Thus, no close tolerances are necessary in the manufacture of the rotary tool driver 10 of the invention.

To release the rotary tool 78 of the invention from the new and improved tool driver 10 of the invention, the process is reversed.

Tool driver 10 may be totally "field strippable" for sterilization purposes whenever desired, by utilizing pins 52 and 54 which are removable whenever desired. By removing the pin 52 which secures ring 30 to rod 32, ring 30 may be removed from rod 32 and tubular handle 26 may be removed from rod 32 by passing ring 30 and handle 26 over collate 20. Similarly, by removing pin 52 which secures ring 28 to rod 32 and secures head 18 and rod 32 together, head, rod 32, spring 58 and ring 28 may be disassembled in to separate integral pieces. Similarly, by receiving pin 54 trigger 24 can be disassembled from head 18 by the removal of pin 54.

Once totally disassembled, tool driver 10 is in a number of pieces that can be easily cleaned and sterilized. Sterilized pieces can then be easily reassembled by repositioning pins 52 and 54 as disclosed. In a specific embodiment, pins 52 and 54 may be conventional screws having a head at one end and threads at the opposite end. Alternatively, pins 52 and 54 may be any of the removable pins taught in the prior art. The trigger 24 is urged against spring 58 toward end 36 of the rod 32 withdrawing the pins 92 into the pin holes 90, the rotary tool 78 is rotated about the axis 22 so as to position the diametral bar 60 in the groove 74 and the rotary tool 78 can then be separated by moving the rotary tool relative to the tool driver 10 axially thereof and a new rotary tool 78 can be installed as above described.

By the invention, there is provided a new and improved tool driver which can be used with rotary tools of all types, including acetabular cups, patella cutters, reamers and the like. The new and improved tool driver of the invention holds rotary tools coaxially of the longitudinal axis with preciseness such that all of the cutting edge of the rotary tools function as designed. The new and improved tool driver of the invention can be utilized with rotary tools of all sizes and can be used with rotary tools of the type which collect milled bone tissue and other debris for use as filler. The new and improved tool driver and the tools of the invention can be easily cleaned, sterilized and reused, are easy and convenient to use, and can be manufactured without holding any close tolerances and yet achieve exact coaxial rotation of the rotary tool.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto.

What is claimed is:

1. A tool driver comprising a shaft having a longitudinal axis and opposite ends, a boss at one of said shaft ends, a tool collet at the other of said shaft ends, said boss having a bayonet type latch mechanism therein, said latch mechanism having an axially extending inwardly tapered bore extending from said one end coaxially of said shaft into said boss, said tapered bore being adapted to receive a coaxially located disc of a tool to be connected to said tool driver within said tapered bore, said tapered bore and said tool disc coaxially centering said tool on said axis of said tool driver.

2. The tool driver of claim 1 wherein said bayonet type latch mechanism comprises a primary groove extending diametrically of said boss, said primary groove having a width sufficient to receive a mounting bar extending diametrically of a rotary tool to be positioned therein, and a secondary diametral groove circumferentially spaced therefrom, said secondary groove also having a width sufficient to receive said tool mounting bar therein, said primary groove having bottom upstanding sides and an open top, said secondary groove having a bottom in the same plane as said primary groove bottom, one upstanding side remote from said primary groove and a top.

3. The tool driver of claim 2 wherein said secondary groove bottom and said secondary groove top being tapered toward said upstanding side.

4. The tool driver of claim 3 wherein said tapered bore has a bottom in the same plane as said primary and secondary groove bottoms, said bore and said primary groove being both accessible from the distal end of said boss, whereby the diametrically extending mounting bar and disc of a tool may be positioned in said primary groove and bore and rotated a partial rotation into said secondary groove.

5. The tool driver of claim 1 wherein a trigger is slideably positioned on said shaft and movable between an at rest position in which said trigger abuts said boss and a position remote therefrom, said trigger being urged toward said boss.

6. The tool driver of claim 2 wherein said boss has a surface opposite said one shaft end, a trigger being slidably positioned on said shaft and movable between an at rest position in which said trigger abuts said opposite boss surface and a position remote therefrom, said trigger being urged toward said boss, said trigger having a pair of pins extending therefrom, said boss having a pair of pin holes in said boss extending axially thereof, said pin holes being between said primary and secondary groove bottoms and extending between said opposite boss surface and said primary and secondary groove bottoms, said boss surface opposite said one shaft end, said pins being positioned within said pin holes in said boss, said pins extending through said boss into said primary and secondary grooves when said trigger is in its at rest position.

7. The tool driver of claim 6 wherein said pins are tapered thereby adjusting the distance between said pins and said upstanding side of said secondary groove.

8. The tool driver of claim 3 further comprising a tool having an open back, a bar diametrically extending across said open back of said tool, a disc on said bar coaxial of said cutting edge and medial of said bar ends, said bar being in said secondary groove and held fast between said secondary groove bottom and said secondary groove top and between said pin and said upstanding side of said secondary groove.

9. The tool driver of claim 8 wherein said tool being maintained coaxially of said tool driver by the engagement between said disc and said tapered bore, said tool driver being prevented from rotating about said axis by engagement between said upstanding side of said secondary groove and said pin, said tool being incapable of axial movement of said tool driver by engagement between said secondary groove bottom and top, said tool being held against lateral or transverse movement of said tool driver by the engagement between said disc and said tapered bore.

10. The tool driver of claim 5 wherein said trigger has a trigger boss at one of said ends, said trigger boss and said boss at one of said shaft ends being approximately the same size, pins being secured to said trigger boss.

11. The tool driver of claim 1 further comprising a handle on said shaft, said handle being freely rotatable about said shaft independently thereof.

12. A tool driver comprising a shaft having a longitudinal axis and opposite ends, a boss at one of said shaft ends, a tool collate at the other of said shaft ends, said boss having a bayonet type latch mechanism therein, said latch mechanism having an axially extending inwardly tapered bore extending from said one end of said shaft into said boss, said tapered bore being coaxial of said shaft, said boss having a rotary lock groove therein, one portion of said lock groove communicating with said one end and diametrically opposite side portions of said boss, a second portion of said lock groove being within said boss and communicating only with said one groove portion of said lock and said diametrically opposite side portions of said boss, said one portion of said lock groove extending diametrically of said tapered bore on opposite sides thereof, said tapered bore and said lock groove being adapted to receive a coaxially located disc of a tool to be connected to said tool driver wherein the coaxially located disc may be received within said tapered bore and a tool mounting bar extending diametrically of said tool may be received in said one portion of said lock groove from said one shaft end, the tool mounting bar being secured to said tool driver in said second portion of said lock groove upon said tool being rotated a partial revolution about said axis relative to said tool driver.

13. A tool driver comprising a shaft having a longitudinal axis and opposite ends, a boss at one of said shaft ends, a tool collet at the other of said shaft ends, said boss having a bayonet type latch mechanism therein, said latch mechanism having an axially extending inwardly tapered bore extending from said one end coaxially of said shaft into said boss, said tapered bore being adapted to receive a coaxially located disc of a tool to be connected to said tool driver within said tapered bore, said tapered bore and said tool disc coaxially centering said tool on said axis of said tool driver, a trigger slidably positioned on said shaft and moveable between an at rest position in which said trigger abuts said boss and a position remote therefrom, a spring and a ring on said shaft, said spring being between said trigger and said ring, said ring being secured to shaft by a removable pin, said spring biasing said trigger against said boss, a handle on said shaft, said handle being freely rotatable about said shaft independently thereof between said removable pin and a second removable pin connected to said shaft.

14. The tool driver of claim 13 wherein said bayonet type latch mechanism comprises a primary groove extending diametrically of said boss, said primary groove having a width sufficient to receive a mounting bar extending diametrically of rotary tool to be positioned therein, and a secondary diametral groove circumferentially spaced therefrom, said secondary groove also having a width sufficient to receive said tool mounting bar therein, said primary groove having bottom upstanding sides and an open top, said secondary groove having a bottom in the same plane as said primary groove bottom, one upstanding side remote from said primary groove, and a top.

15. The tool driver of claim 14 wherein said trigger has a pair of pins extending therefrom, said pins being positioned within said holes and said boss, said pins extending through said boss into said secondary groove when said trigger is in its at rest position.

16. The tool driver of claim 14 wherein said secondary groove bottom and said secondary groove top being tapered toward said upstanding side.

17. The tool driver of claim 15 wherein said pins are tapered thereby adjusting the distance between said pins and upstanding side of said secondary groove.

18. The tool driver of claim 15 further comprising a tool having an open back, a bar diametrically extending across said open back of said tool, a disc on said bar coaxial of said cutting edge and medial of said bar ends, said bar being in said secondary groove and held fast between said secondary groove bottom and said secondary groove top and between said pin and said upstanding side of said secondary groove.

19. The tool driver of claim 18 wherein said tapered bore has a bottom in the same plane as said primary and secondary groove bottoms, said bore and said primary groove being both accessible from the distal end of said boss, whereby the diametrically extending mounting bar and disc of a tool may be positioned in said primary groove and bore and rotated a partial rotation into said secondary groove.

\* \* \* \* \*